United States Patent [19]
Tarjan et al.

[11] Patent Number: 6,091,977
[45] Date of Patent: *Jul. 18, 2000

[54] SENSOR

[75] Inventors: Peter P Tarjan, Miami; Monica Kaufer-Braverman, Plantation, both of Fla.; Leonard L. Rasquinha, Issaquah, Wash.

[73] Assignee: The University of Miami, Miami, Fla.

[*] Notice: This patent is subject to a terminal disclaimer.

[21] Appl. No.: 09/166,335

[22] Filed: Oct. 5, 1998

Related U.S. Application Data

[62] Division of application No. 08/843,301, Apr. 14, 1997, Pat. No. 5,817,030, which is a continuation of application No. 08/667,374, Jun. 21, 1996, abandoned, which is a continuation of application No. 08/418,565, Apr. 7, 1995, abandoned.

[51] Int. Cl.⁷ .................................................. A61B 5/0492
[52] U.S. Cl. ........................... 600/372; 600/393; 600/395
[58] Field of Search ........................... 600/372, 382–386, 600/391–397; 607/149, 152, 148; 606/32

[56] References Cited

U.S. PATENT DOCUMENTS

| | | |
|---|---|---|
| 3,641,993 | 2/1972 | Gaarder et al. . |
| 3,774,593 | 11/1973 | Hakata et al. . |
| 4,359,724 | 11/1982 | Zimmerman et al. . |
| 4,725,824 | 2/1988 | Yoshioka . |
| 5,295,482 | 3/1994 | Clare et al. .............................. 128/639 |
| 5,520,683 | 5/1996 | Subramaniam et al. .................. 606/32 |
| 5,817,030 | 10/1998 | Tarjan et al. ............................ 600/546 |

FOREIGN PATENT DOCUMENTS

| | | | |
|---|---|---|---|
| 1219642 | 3/1987 | Canada | ................................... 606/32 |

*Primary Examiner*—Lee Cohen
*Attorney, Agent, or Firm*—Pillsbury Madison & Sutro LLP

[57] ABSTRACT

A plurality of locally sensitive, far-field immune sensors are mounted in mutually spaced relation on the exterior of the body of a subject to detect electrical signals associated with voluntary skeletal muscle activity in the immediate physical vicinity of the sensors. The detected signals are used to determine which, if any, of a predetermined series of voluntary skeletal muscle maneuvers is performed by the subject. A signal bearing a predetermined relationship to the maneuver is then transmitted to a device to be controlled based on which maneuver the subject has performed. Also disclosed are a novel sensor and a method of making same.

5 Claims, 7 Drawing Sheets

SENSOR

This is a divisional of application Ser. No. 08/843,301, filed on Apr. 14, 1997, now U.S. Pat. No. 5,817,030 issued Oct. 6, 1998, which is a Continuation of application Ser. No. 08/667,374, filed on Jun. 21, 1996, now abandoned, which is a Continuation of application Ser. No. 08/418,565, filed on Apr. 7, 1995, now abandoned.

FIELD OF THE INVENTION

The invention relates to the control of a device according to electrical signals generated by muscle activity. More particularly, the present invention relates to an apparatus and method for controlling a device by classifying patterns of skeletal muscle activity detected by a plurality of spaced, locally-sensitive, far-field immune sensors on the surface of the face and forehead region of a human subject.

BACKGROUND

Analysis of electrical signals produced by muscle activity has been found useful in a variety of monitoring and control applications. One of the most familiar is the electrocardiogram or "ECG" which utilizes a plurality of electrodes in contact with the surface of the skin at various locations on the human body to detect electrical waveforms indicative of cardiac activity. Analysis of such waveforms is useful in the diagnosis of many pathological conditions of the heart. Peter P. Tarjan, one of the present co-inventors, has also experimented with sensors and triangulation techniques for cardiac arrhythmia detection in canines as presented in 1987 at the World Symposium on cardiac Pacing in Jerusalem, Israel and at the North American Society for Pacing and Electro-Physiology in Boston, Mass.

It has also been known to detect the electrical activity of skeletal muscles, such as those in the area of the eyelids or eyebrows, in order to monitor an individual's state of consciousness or sleep. U.S. Pat. No. 4,359,724 to Zimmerman et al. relates to an eyelid movement detector which employs a bipolar electrode placed over each eyebrow of a person. The electrodes are coupled to a circuit which includes a timer which is reset in response to eyelid activity detected by the electrodes. If the timer fails to be reset within a predetermined time interval, it activates a warning device, such asian audible alarm, to warn the person that they are becoming drowsy. An alternative embodiment uses a third electrode positioned on the forehead between the other two electrodes to provide a reference signal level for improved noise immunity.

Efforts have also been made to control devices, such as the actuators of an artificial limb, according to electrical signals derived from electrodes responsive to skeletal muscle activity. Bipolar electrodes have been used by Stephen Jacobsen to detect myopotentials of the trapezius and deltoids for controlling the "Utah" artificial human arm and other prosthetic devices. However, biological control of prostheses or other non-biological systems has presented obstacles which have not been satisfactorily overcome.

Sequential input systems such as the oral pneumatic "sip and puff" devices used by some quadraplegics can be adapted for use with an arbitrarily large set of input commands but become progressively slower to use as the size of the command set increases. In systems wherein commands are determined by combinations of inputs, the number of control states which can be effected is limited by the available number of distinct biological input conditions which can be voluntarily produced by a subject and reliably recognized by the system to be controlled. While controls based on voice inputs have advanced remarkably in recent years and offer the ability to recognize large numbers of commands, voice-activated systems are not suitable for many applications such as those in aircraft cockpits or on the floor of a factory where a considerable amount of acoustic background noise may be present. Sensing of myopotentials can provide excellent immunity from such external environmental influences but has been restricted in practical utility. One problem has been the relatively small number of control input conditions discriminable using skin surface mounted electrode arrays of a given size and mutual spacing. This has been due to the tendency of known skin surface mounted electrodes to respond to the electrical activity of not only the muscle in the immediate vicinity of the electrode but also to that from relatively distant locations. For example, bipolar electrodes of the type used in Zimmerman et al. '724 are known to respond to electrical activity of muscle tissue located a considerable distance from that immediately underlying the electrode itself. This necessitates a relatively wide separation between electrodes in order to provide discriminable differences in their responses to different voluntary muscle activities. As a consequence the number of distinct "commands" discriminable by an electrode array of a given number of electrodes and mutual spacing is limited. In theory, this limitation can be overcome by using invasive electrodes.

Various types of implanted or invasive electrodes are known which respond to the local electrical activity of a nerve or muscle while not responding to the activity of closely adjacent nerves or muscles. Indeed, a microelectrode penetrating the surface of the body can be located to respond only to the activity of a single neuron or myofibril. However, the use of implanted or invasive electrodes is disfavored other than for short term laboratory or clinical use because they can cause discomfort and pose a risk of infection.

SUMMARY OF THE INVENTION

In view of the foregoing problems and limitations of the prior art, there is a need for a non-invasive, externally mountable sensor capable of detecting the electrical activity of skeletal muscles in the immediate area underlying the sensor to a depth of a few millimeters, but which is substantially insensitive to electrical activity occurring elsewhere. Such a sensor is referred to herein and in the claims as being "locally sensitive, far-field immune." There is also a need for an apparatus and method for controlling a device based on biological inputs which provides the ability to enter commands rapidly, but which, unlike voice input systems, is suitable for operation in the presence of high levels of acoustic noise. Further, there is a need for such an apparatus and method capable of implementation with non-invasive sensors while not requiring a wide mutual spacing between sensors in order to define distinct commands.

The invention achieves these and other objects and advantages by providing an externally mountable, locally sensitive, far-field immune sensor which includes an interior conductive region spaced from and surrounded by a continuous middle conductive region which, in turn, is spaced from and surrounded by a continuous exterior conductive region with the interior region being electrically coupled to the exterior region, preferably through a short circuit. It has been found that such a sensor responds predominantly to the activity of muscle directly beneath its surface and is substantially non-responsive to the activity of surrounding muscle tissue. In a preferred form, the interior conductive region of the sensor is provided in the form of a circle and the middle and exterior regions formed as circular rings positioned concentrically with respect to the interior circle with gaps between the three concentric elements. This geometry renders the electrode omnidirectional in a plane and responsive in substantially real time to the activity being detected.

A further aspect of the invention provides an apparatus and method for controlling a device based on inputs derived from the electrical activity of skeletal muscles as sensed by a plurality of electrodes which are preferably of the type referred to above. It has been discovered that an array of such electrodes, positioned on the surface of the skin on the face and forehead of a human subject in relatively close proximity to one another is capable of detecting a plurality of distinct electrical patterns which can be discriminated and uniquely associated with members of a set of commands for controlling a device such as a prosthesis, a biofeedback signalling device, a vehicle or other machine.

These and other aspects and advantages of the present invention will be made even more clear to those of ordinary skill in the art upon review of the following detailed written description of a preferred embodiment of the invention taken in conjunction with the appended drawings which are briefly described below and in which like reference numerals are used to designate like items.

DETAILED DESCRIPTION OF THE INVENTION

Figure 1:
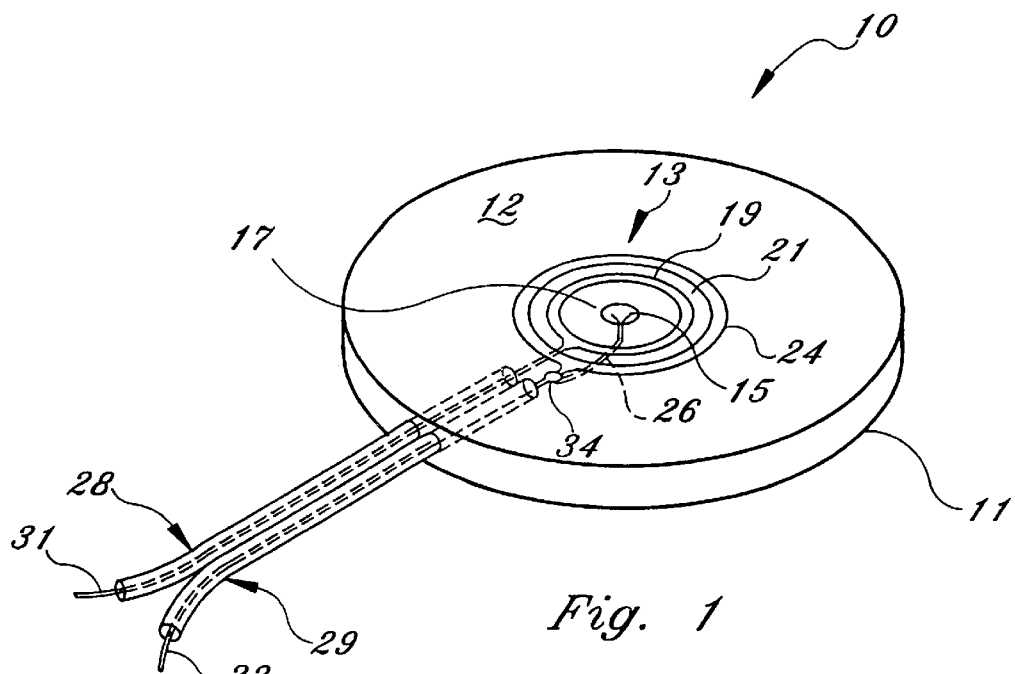
FIG. 1 is a perspective view of a first preferred sensor for use with the present invention.

Referring now to FIG. 1, there is illustrated by way of example, a preferred embodiment of an sensor 10 suitable for use in connection with the present invention. Sensor 10 includes a disk-shaped, electrically insulating mounting body 11 of silicone rubber or other compliant, electrically insulating material. Mounting body 11 defines a generally planar skin contact surface 12 into which an electrically conductive sub-assembly 13 is substantially flushly embedded. Sub-assembly 13 includes an electrically conductive inner pad 15 separated by a first insulating annulus 17 from a continuous middle loop electrode 19. Loop electrode 19 is surrounded by a second insulating annulus 21 which, in turn, is surrounded by a continuous exterior loop electrode 24. In order to provide sensor 10 with uniform directionality of response in a plane, inner pad 15 is preferably round and circular in shape and loop electrodes 19 and 24 are formed as circular rings located concentrically with respect to pad 15 as well as with respect to one another. In applications where uniform directionality of response is not required or where it is desired to provide enhanced or reduced sensitivity in certain directions, pad 15 and/or loop electrodes 19 and 24 can be formed in other shapes and/or located off center with respect to one another provided that at least some mutual spacing is maintained between pad 15 and continuous loop electrodes 19 and 24.

In order to render sensor 10 sensitive substantially only to the electrical activity of only that muscle tissue which substantially immediately underlies the skin surface which sub-assembly 13 is placed in contact with, inner pad 15 and exterior 24 are electrically coupled to one another, preferably by a short circuit. In the preferred embodiment of FIG. 1, this is achieved by a jumper wire 26 having one end connected to pad 15 and its opposing end connected to exterior loop electrode 24. The portion of jumper wire 26 which crosses middle loop electrode 19 is electrically insulated in order to electrically isolate loop electrode 19 from both pad 15 and exterior loop electrode 24. Sensor 10 is provided with a pair of insulated lead wires 28, 29. The conductor 31 of lead wire 28 is connected directly to middle loop electrode 19 while the conductor 32 of lead wire 29 is connected electrically in common with both inner pad 15 and exterior loop electrode 24. This is conveniently accomplished with a single electrical connection 34 by attaching the conductor 32 of lead wire 29 directly to jumper wire 26. To avoid detachment of lead wires 28 and 29 from sensor element 13, strain relief is preferably provided by anchoring wires 28, 29 to mounting body 11. This may readily be achieved by insert molding or use of an adhesive. Concentricity of pad 15 and loop electrodes 19 and 24 may be assured by various means, including use of a mounting body 11 which is molded or otherwise preformed with a recess for locating pad 15 and appropriately sized and centered channels for receiving loop electrodes 19 and 24.

Sub-assembly 13 may also be fabricated by positioning a cylindrical rod of brass or other suitable electrically conductive material in the center of a first length of hollow cylindrical tubing. While maintaining the longitudinal axes of the rod and tubing in alignment with one another, the space between the exterior wall of the rod and the interior wall of the tubing is filled with a polymerizable liquid electrical insulating material such as epoxy or silicone in order to form first insulating annulus 17. When the polymer is sufficiently set, the rod and tubing are centered inside a second length of hollow, cylindrical conductive tubing which has an inside diameter larger than the outside diameter of the first length of tubing. The space between the first and second lengths of tubing is then likewise filled with silicone or other suitable insulating material which is permitted to set in order to form second insulating annulus 21. With a diamond saw or other suitable cutting instrument, thin slices of the rod and tubing structure are then made perpendicular to the longitudinal axes of the rod and tubing to form individual sensor elements 13 which may then be embedded in or adhesively secured to mounting body 11 after securing a jumper wire 26 in place on the side opposite skin contact surface 12. In the preferred embodiment the rod forming inner pad 15 may suitably be about one millimeter or less in diameter while the tubing forming middle conductive ring 19 and exterior conductive ring 24 may each suitably have wall thicknesses of about one half millimeter and outside diameters of about two and four millimeters, respectively.

Figure 2A:
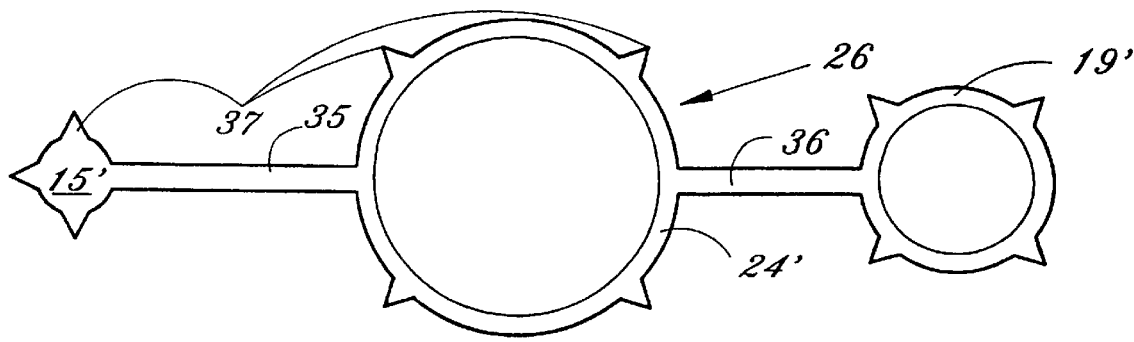
FIG. 2A illustrates a blank useful in fabricating a second preferred sensor according to the present invention.

In an alternative embodiment, a subassembly 13' may be fabricated from a thin sheet of stainless steel or other suitable material, by photoetching, stamping, laser cutting or die cutting same to form a unitary, flat blank 26 of a shape such as that shown for illustration in FIG. 2A. Blank 26 includes an inner pad 15' and a middle loop electrode 19' which are attached to an exterior loop electrode 24' by a permanent arm 35 and a severable arm 36. Preferably, pad 15' and loop electrodes 19' and 24' are each provided with several bendable projections or prongs 37 to assist in securing pad 15' and loop electrodes 19' and 24' to electrode mounting body 11'.

Figure 2B:
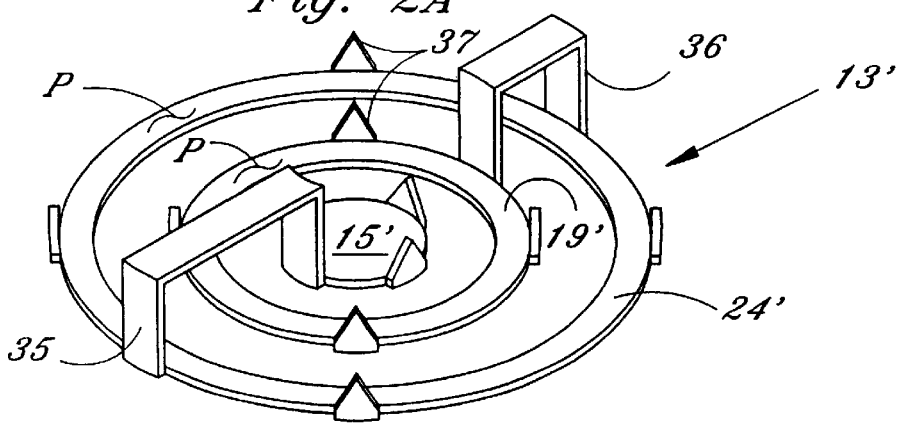
FIG. 2B is a perspective view of the subassembly of FIG. 2A after folding.
Figure 2C:
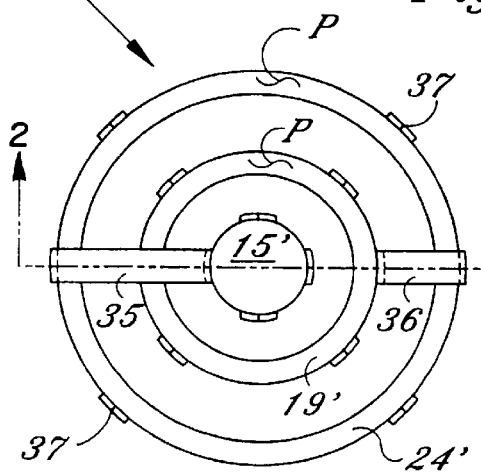
FIG. 2C is a top view of the folded blank of FIG. 2B.
Figure 2D:
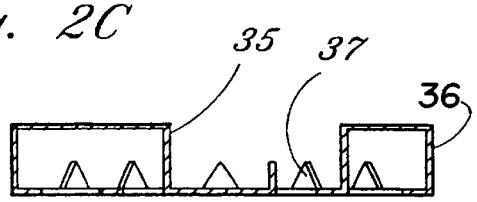
FIG. 2D is a sectional view taken along line 2—2 of FIG. 2C.
Figure 2E:
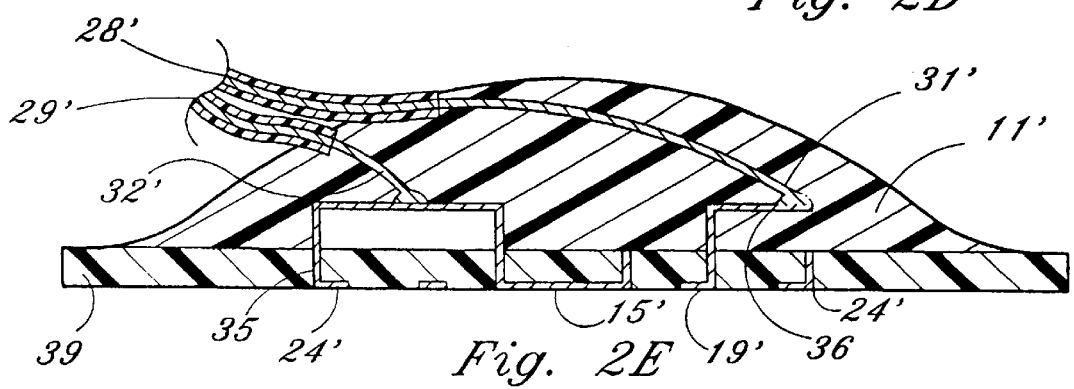
FIG. 2E is a sectional view of a completed second embodiment of a sensor according to the present invention.

Blank 26 is then folded in the manner illustrated in FIGS. 2B, 2C and 2D. Severable arm 36 is first bent to locate middle loop electrode 19' interiorly of exterior loop electrode 24' such that the two loop electrodes 19' and 24' lie in a common plane P, and are positioned concentrically with respect to one another. Permanent arm 35 is then bent to locate interior pad 15' interiorly of middle loop electrode 19' such that it also lies in plane P and is centered with respect to loop electrodes 19' and 24'. Prongs 37, if provided, are bent at their leases to project away from plane P, preferably at right angles as shown. The conductor 31' of a lead wire 28' is then welded, soldered, brazed or otherwise suitably secured electrically and mechanically to a portion of severable arm 36 which remains connected to middle loop electrode 19'. The conductor 32' of a second insulated lead wire 29' is similarly secured to the permanent arm 35. Permanent arm 35 forms a bridging connection between pad 15' and exterior loop electrode 24' and thus eliminates the need for connection of a separate jumper wire (such as the jumper wire 26 in the embodiment of FIG. 1) to join those elements. After lead wires 28' and 29' have been attached, folded blank 26 is then positioned within a compliant electrically insulating mounting body 11' which may be formed by any of a number of techniques such as molding or casting. Preferably, mounting body 11' is molded, cast or otherwise formed to encapsulate folded blank 26' and at least a terminal portion of leads 28' and 29' within a unitary structure. Alternatively, a portion of mounting body 11' could be formed as a preformed base 39 having preformed recesses for receiving and centering pad 15' and loop electrodes 19' and 24'. In order to electronically isolate loop electrodes 19' and 24' from one another, severable arm 36 is severed. If desired, severing of arm 36 may be carried out after subassembly 13' has been secured within mounting body 11' by using a small cutting or grinding tool to cut through a small part of mounting body 11' as well as through severable arm 36. Once severable arm 36 has been cut, the remaining hole in mounting body 11' can be plugged or filled in with a suitable electrically insulating sealant.

Figure 3:
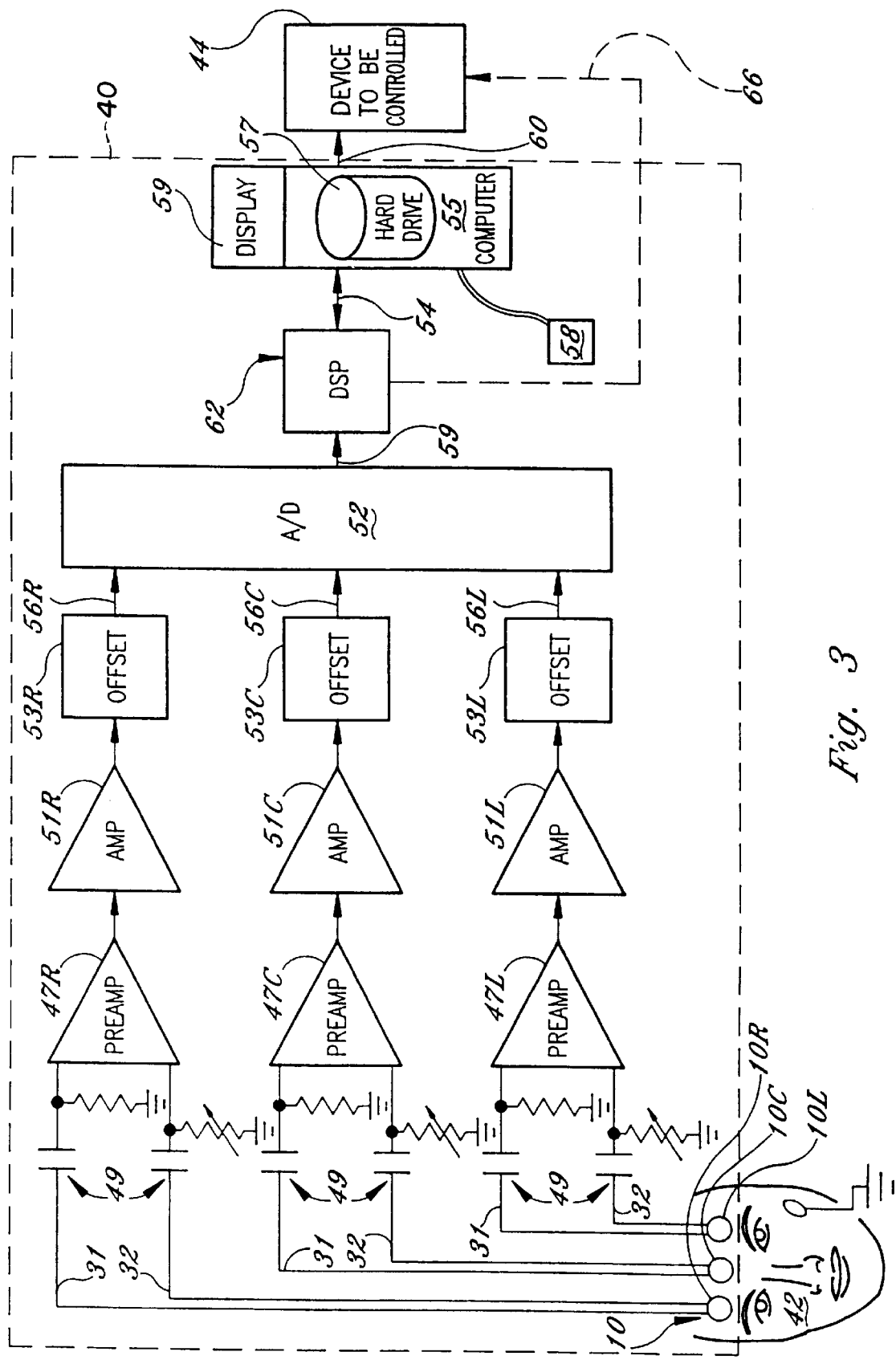
FIG. 3 is a block diagram of the apparatus of the invention illustrating a preferred placement of a plurality of the sensors of FIG. 1 on a human subject.
Figure 5:
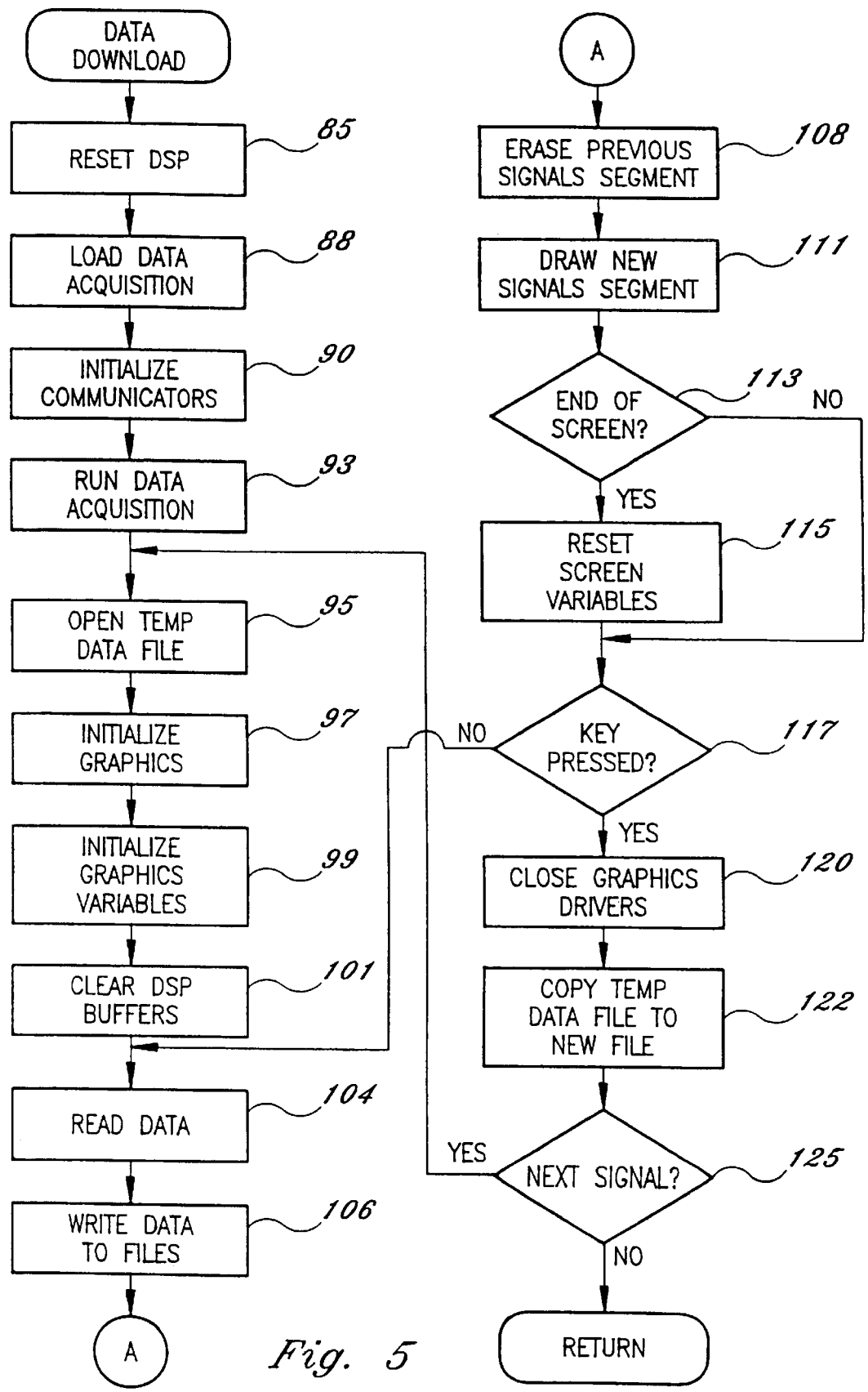
FIG. 5 is a flow chart illustrating a data downloading routine executed by the computer of FIG. 3.
Figure 6:
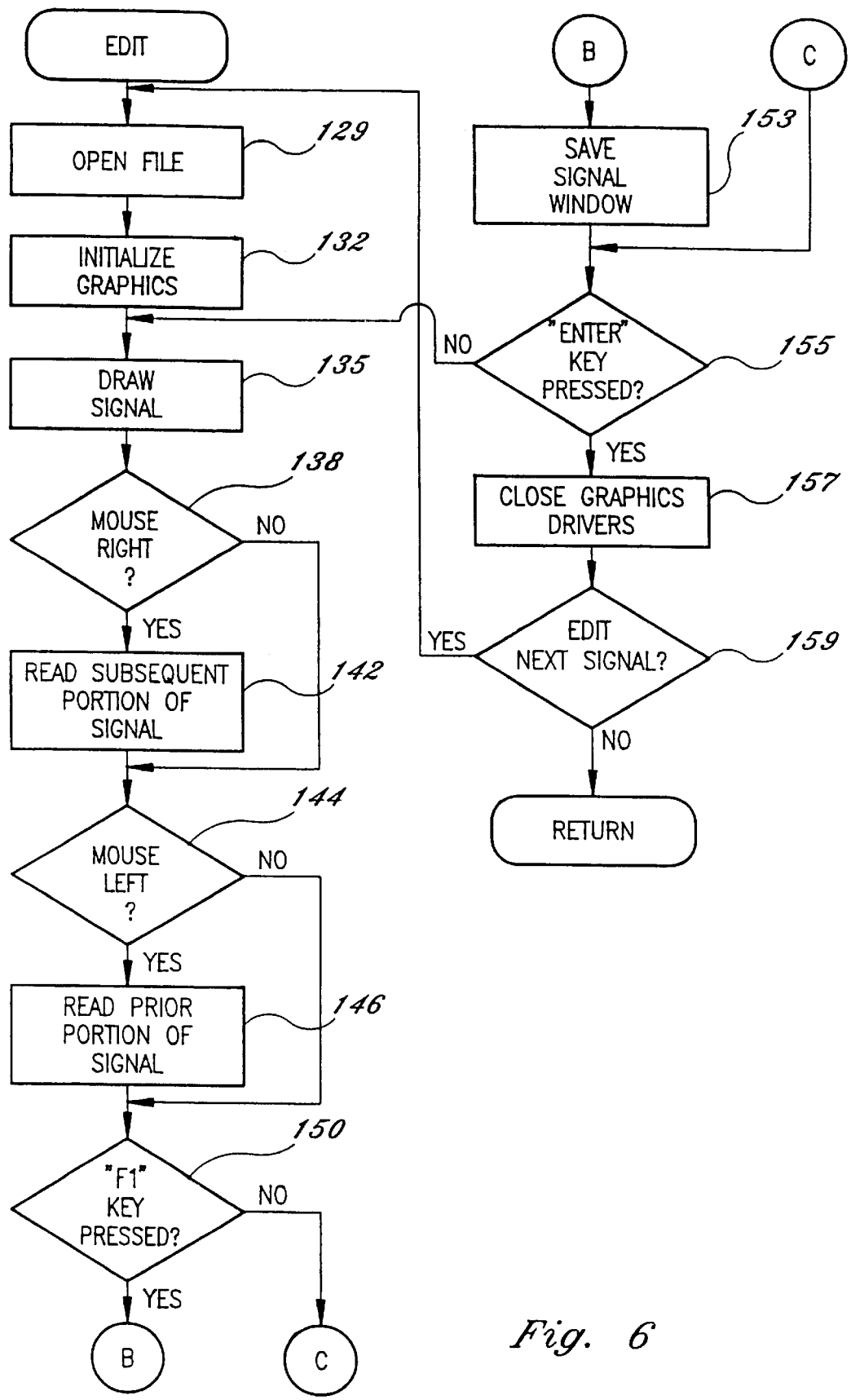
FIG. 6 is a flow chart illustrating an editing routine executed by the computer of FIG. 3.

An apparatus 40 which permits a human subject 42 to control a device such as a prosthesis or other machine according to voluntary muscle activity is illustrated in FIG. 3. Apparatus 40 includes a plurality of sensors 10 secured to the surface of the skin of subject 42. Sensors 10 are positioned mutually spaced from one another by a distance sufficient to permit each sensor 10 to respond substantially independently to the electrical activity of skeletal muscle underlying each sensor 10. In the preferred embodiment shown, right and left sensors 10R and 10L are positioned supraorbitally on the forehead above the right and left eyes, respectively of subject 42 while a sensor electrode 10C is positioned between the right and left sensors 10R and 10L at the midline on the forehead above the bridge of the nose of subject 42. As an aid to their proper positioning and securement on the exterior body surface of subject 42, sensors 10R, 10C and 10L may conveniently be mounted in a desired mutually spaced relationship on a headband, visor or hatband (not shown). The conductors 31 and 32 of sensors 10R, 10C and 10L are connected to respective ones of a series of preamplifiers 47R, 47C and 47L by way of a series of RC networks 49 selected to match the impedances of electrodes 10R, 10C and 10L to preamplifiers 47R, 47C and 47L, respectively. Preamplifiers 47R, 47C and 47L may each suitably comprise balanced differential, d.c.-coupled amplifiers such as model 176K available from Calex of Concord, Calif. or equivalent. Each preamplifier 47R, 47C and 47L is coupled to a corresponding one of a series of amplifiers 51R, 51C and 51L. In the preferred embodiment, the overall voltage gain factor applied by each one of preamplifiers 47R, 47C and 47L and its respective amplifier 51R, 51C and 51L is about five thousand (5,000×). Amplifiers 51R, 51C and 51L are in turn coupled to respective inputs of an analog-to-digital (A/D) converter board 52 by way of a series of offset circuits 53R, 53C and 53L to remove any d.c. components from the analog input signals 56R, 56C and 56L applied to A/D converter 52 and scale those signals suitably to avoid saturation of A/D converter 52. In the preferred embodiment, A/D converter 52 has a single, 8-bit multiplexed digital output 59 which is applied to the input of a programmable digital signal processor (DSP) 62 which may suitably comprise a model DSP56000 available from Motorola or equivalent. A detachable cable 54 connects the output of DSP 62 to a personal computer 55 which includes a hard drive 57 or other suitable memory, a pointing device such as a mouse 58 and preferably a CRT or other suitable display 59. As will be explained below, computer 55 is an optional component of apparatus 40 which may be used to develop suitable templates, but which can be disconnected and removed when apparatus 40 is in actual use for controlling device 44. If it is desired to utilize computer 55 during control operations, computer 55 may be coupled to a device 44 to be controlled by way of a suitable communication path 60 which may comprise a hard wired, optical, RF or other suitable link.

In operation, subject 42 performs one or more of a series of voluntary maneuvers which stimulate muscle tissue underlying one or more of sensors 10R, 10C and/or 10L. Each sensor 10R, 10C and 10L detects the local electrical activity, if any, associated with a given maneuver while strongly attenuating signals emanating elsewhere. The pattern of electrical activity detected by sensors 10R, 10C and 10L is digitized, processed and compared to a series of predefined templates, each one of which corresponds to a particular command or command sequence. If a suitable degree of correspondence between the template and the digitized pattern is detected, the command or series of commands is generated and applied to the device 44 to be controlled.

In the preferred embodiment, a series of commands may be defined according to whether subject 42 squints one or both eyes either once or twice. For example, a single squint of the left eye may be assigned a binary value of 1000 according to a code in which the two most significant bits reflect left and right squints occurring singly and the two least significant bits reflect a second squint of one or both eyes activity. An example of such a code is given in Table I below.

TABLE I

| VOLUNTARY MANEUVER | FIRST EVENT | | SECOND EVENT | |
|---|---|---|---|---|
| | L | R | L | R |
| squint left | 1 | 0 | 0 | 0 |
| squint right | 0 | 1 | 0 | 0 |
| squint left then right | 1 | 0 | 0 | 1 |
| squint right then left | 0 | 1 | 1 | 0 |
| squint both once | 1 | 1 | 0 | 0 |
| squint both twice | 1 | 1 | 1 | 1 |
| squint left twice | 1 | 0 | 1 | 0 |
| squint right twice | 0 | 1 | 0 | 1 |

The system may also be programmed to distinguish between squints (momentary closures of the eyelid) and raising either one or both eyebrows which causes the muscles to move in a manner opposite that of squinting. Once apparatus 40 determines which, if any, voluntary maneuver from Table I, for which a template has been defined, has been performed by subject 42, a command or sequence of commands associated with the binary code of that maneuver is generated and delivered to the controlled device 44 by way of communication path 60 or 66.

Sensors 10R, 10C and 10L detect the electrical activity of the skeletal muscle tissue substantially underlying each respective one of them. While only two sensors 10L and 10R, could be used to detect the eye squinting maneuvers listed in Table I, the use of additional central sensor 10C is preferred in order to improve the ability of apparatus 40 to reliably distinguish one maneuver from another. Sensors 10R, 10C and 10L each pass a weak electrical signal through respective RC networks 49 to respective, high impedance preamplifiers 47R, 47C and 47L. Amplifiers 51R, 51C and 51L receive signals from preamplifiers 47R, 47C and 47L and amplify them further. Any d.c. components of the signals are removed by offset circuits 53R, 53C and 53L which provide properly scaled zero to five volt analog signals 56R, 56C and 56L. Signals 56R, 56C and 56L are applied to an 8-bit analog-to-digital converter 52 whose multiplexed output 59 is applied to digital signal processor 62. The programming and operation of DSP 62 and computer 55 will now be explained in further detail with reference to the flow charts of FIGS. 3 through 8.

As illustrated in FIG. 3, digital signal processor (DSP) 62 receives from A/D 52 digitized representations of the analog signals emanating from sensors 10R, 10C and 10L while subject 42 performs any of the maneuvers listed in Table I. The data acquisition routine of FIG. 3 commences with the steps of initializing digital signal processor 62 and setting a series of three memory pointers to point to the beginning addresses of the three, 8-bit, 512 byte buffers assigned to receive data from left, right and center electrodes 10L, 10R and 10C, respectively. These steps are indicated at block 70 of FIG. 4. Thereafter, as indicated at 72, an interrupt timer is set to a value appropriate to allow digital signal processor 62 to sequentially sample each channel at the rate of two hundred fifty hertz (250 Hz) as indicated by timer interrupt subroutine 75 which runs continuously. As indicated at block 78, the buffer associated with each channel proceeds to be filled with data until each buffer is full. Thereafter as indicated at 80, the signal data stored in each buffer is stored in memory. Once data transmission is completed, the memory pointers are reset as indicated at block 82 to again point to the beginning address of the above-referenced buffers to prepare for receipt of the next signal. Running of the data acquisition routine which has just been described can be initiated by a DATA DOWNLOAD routine which runs on computer 55 and which will be described with reference to FIG. 5.

Figure 4:
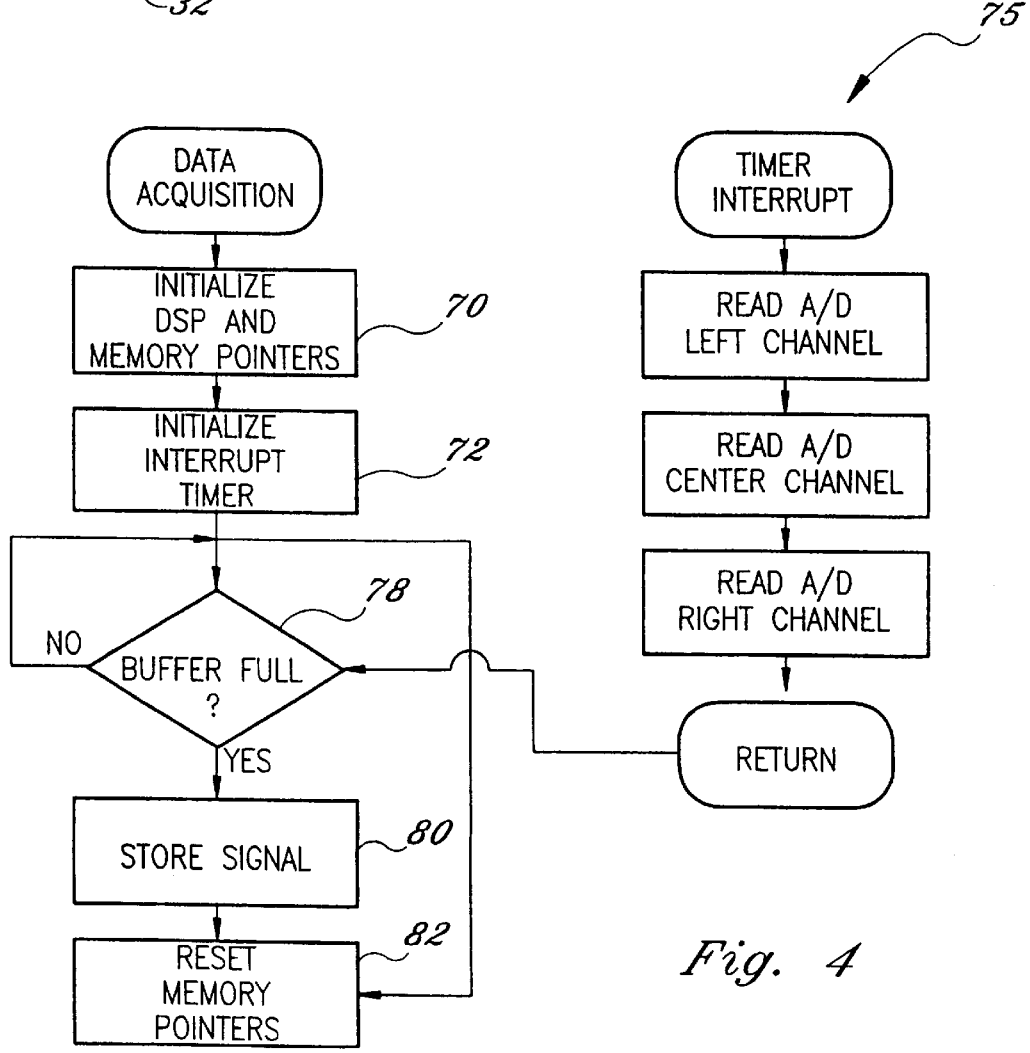
FIG. 4 is a flow chart illustrating the data acquisition routine executed by the digital signal processor of FIG. 3.

At the outset of the DATA DOWNLOAD routine, computer 55 generates a reset command as indicated at 85. This reset command is communicated to digital signal processor (DSP) 62 by way of cable 54 in order to halt any program which may previously have been running on DSP 62. As indicated at block 88, the data acquisition routine of FIG. 4 is then loaded from computer 55 into random access program memory associated with DSP 62. Communications between computer 55 and DSP 62 are initialized as indicated at 90 and the running of data acquisition program on DSP 62 is commenced as indicated at 93. Computer 55 opens a temporary data file, as block 95 indicates, in order to receive signal data stored in memory by DSP 62 pursuant to block 80 of FIG. 4. Optionally, the signal in each channel can be displayed simultaneously on the CRT display 59 associated with computer 55. Preferably, the signals associated with each channel are displayed one above another such that the horizontal axis display 59 represents a time scale common to each channel. Such graphics may conveniently be implemented using conventional graphics software utilities such as the VGA.BGI utility associated with the Borland C++ Ver. 3.1 TurboVision® package available from Borland of Scotts Valley, Calif. If such graphics are used, the graphics utility is initialized, as indicated at 97, and graphics variables are initialized as indicated at 99. To avoid consideration of any spurious signal data which may have been received in the meantime, the data storage buffers associated with digital signal processor (DSP) 62 are then cleared as indicated at 101. Computer 55 then reads the signal data from DSP 62 and writes that data to storage files as indicated at blocks 104 and 106, respectively.

The graphics program loaded onto the hard drive 57 of computer 55 displays a segmental oscillographic representation of the signals associated with each channel. To do so, segments of any signals previously displayed are erased as indicated at block 108. Thereafter, the erased segment is overwritten with new data as indicated at 111 and a check is made at 113 to determine whether the end of the screen has been reached. If so, the screen variables are reset to insure that any new signal data will be displayed beginning at the appropriate starting addresses of the screen as indicated at 115. Provided no keyboard keys are pressed, the program loops back to block 104 to continue displaying data as it is received from the I/O port of computer 55. As block 117 indicates, pressing of a key initiates closing of the graphics drivers and copying of the temporary data file to a new file location as indicated at blocks 120 and 122, respectively. Upon receipt of a new signal, program flow loops back to block 95 whereupon a new temporary data file is opened. Otherwise, program flow returns to the point at which the data download routine was called as indicated at decision block 125. Once a plurality of signal data files have been acquired, those files may optionally be edited for the purpose of discarding any distorted or spurious signals which may have been acquired. Such editing is conveniently performed with the aid of an EDIT routine which will now be described with reference to FIG. 6.

As indicated at 129 the data file to be edited is opened and graphics are initialized as indicated at 132. The signal to be edited is then drawn (i.e., displayed graphically) on display 59 in the manner described above as indicated at 135. The graphics routine establishes a movable data window of a predefined width such as 512 bytes. As indicated by the sequence at blocks 138, 142, 144 and 146 movement of the mouse 58 effectively shifts this window selectively in either of the two opposing directions parallel to the horizontal axis of display 59 in order to include prior or subsequent portions of the signal within the window. In this way, any spurious signals may be excluded from the window. Once the window is positioned as desired, pressing of the "F1" key of computer 55 is checked as indicated at block 150. If the "F1" key is pressed, the present contents of the window are saved for classification by apparatus 40 as indicated at block 153. Otherwise, saving step 153 is skipped and the "ENTER" key is polled as block 155 shows. If the "ENTER" key is pressed, the graphics drivers are closed as indicated at block 157. Otherwise, program flow is redirected to block 135 to permit further editing of the signal. If the operator enters a command indicating a desire to edit the next signal, flow is redirected to block 129 to recommence the editing routine as block 159 indicates. If such a command is not entered, program flow returns to the point from which the edit routine was called. The signal as saved within the window is then processed and classified by comparison with a series of stored templates. These templates are generated with the aid of computer 55 prior to using device 40 for control purposes in a manner which will now be described with reference to the TEMPLATE routine of FIG. 7.

In order to generate a template, computer 55 opens a session file in memory as indicated at block 160. Within the session file is recorded a series of signals detected by way of sensors 10R, 10C and 10L while subject 42 repetitively performs just one of the voluntary maneuvers listed in Table 1. After each signal in the session file is optionally subjected to editing in the manner described above with reference to FIG. 6, the signal is read, smoothed and detrended as indicated at blocks 162, 165 and 167, respectively. In order to perform the smoothing operation of block 165, computer 55 recalculates each of the 512 data points of each signal by setting its magnitude to one-fifth of the sum of its original magnitude plus the magnitudes of the two immediately preceding and the two immediately succeeding data points. The detrending operation of block 167 consists of eliminating any d.c. component of the signal by calculating the mean magnitude value of the signal and subtracting the mean from each byte. As indicated at block 169, the detrended signal is then shifted as necessary to position its magnitude peak in the center of the 512 byte window. Once the foregoing operations have been performed as indicated by block 170 for each signal in the session file, the template for the particular voluntary maneuver performed by subject 42 during the session is defined as indicated at block 172. To do so, computer 55 generates a series of 512 bytes, wherein each byte in the series has a magnitude equal to the arithmetic average of the corresponding bytes of each centered signal in the session. That is, the magnitude of the $n^{th}$ byte of the template is computed as the sum of the magnitudes of the $n^{th}$ bytes in each centered signal divided by the number of signals in the session file. Thereafter, as indicated at block 175, the template for the session file is stored in a series of memory locations whose beginning address is associated with the particular voluntary maneuver performed by subject 42 during the session corresponding to the session file most recently processed. As indicated at block 177, the stored template may optionally be displayed on display 59 in an analog format as described above. As block 180 indicates, the above process is repeated until a template corresponding uniquely to each one of the voluntary maneuvers listed in Table I has been defined and stored in an EPROM associated with DSP 66 or in memory associated with computer 55.

Once a template for each of the voluntary maneuvers listed in Table I has been defined and stored, apparatus 40 may be used by subject 42 to control a prosthesis or other device 44. To do so, digital signal processor 62 executes routines which operate to discriminate the signals received from sensors 10R, 10C and 10L by way of A/D 52 and transmit an appropriate control signal as will now be described with reference to the DISCRIMINATE routine of FIG. 8.

Figure 7:
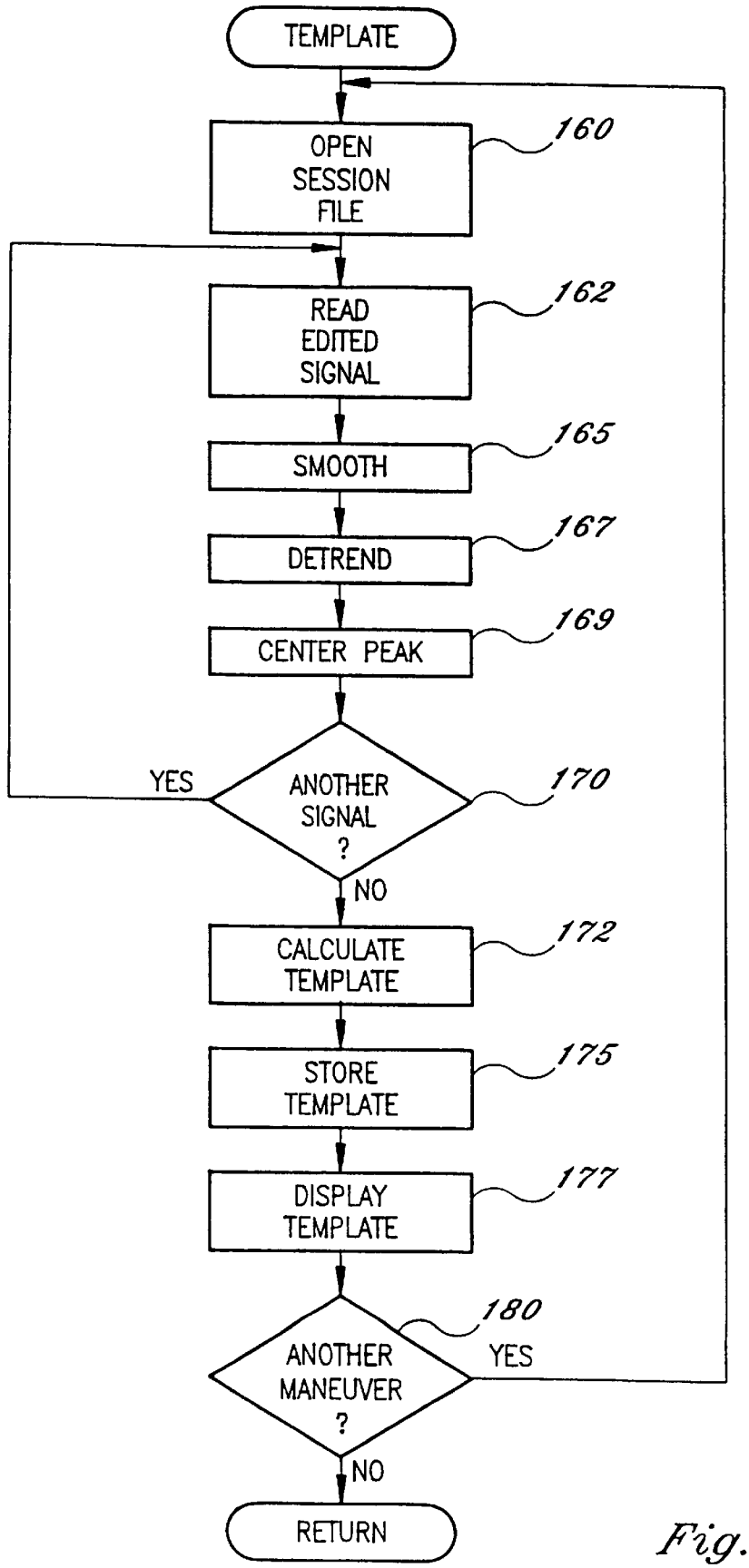
FIG. 7 is a flow chart illustrating a template determination routine executed by the digital signal processor of FIG. 3.
Figure 8:
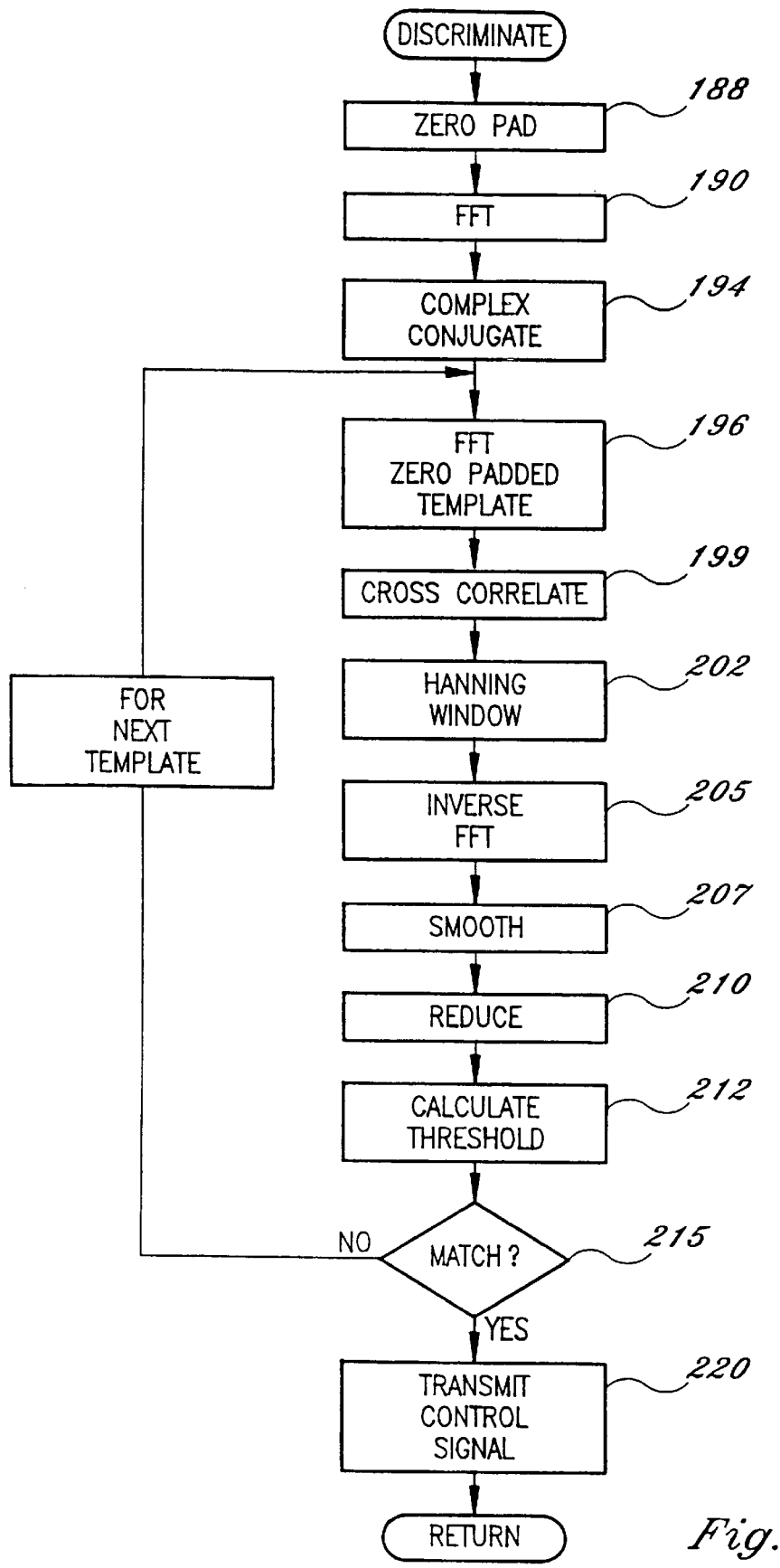
FIG. 8 is a flow chart illustrating a discrimination routine executed by the digital signal processor of FIG. 3.

Each 512 byte signal received from electrodes 10L, 10C and 10 by way of A/D 52 is zero padded by adding an additional 512 bytes of zeros to the end of the signal data as block 188 indicates. This expands each signal to 1024 bytes. It should be noted that in a similar fashion, each template stored in accordance with block 175 of FIG. 7 is also zero padded to 1024 bytes. However, in the case of each template, 512 bytes of zeros are added to the beginning rather than to the end thereof. A Fast Fourier Transform (FFT) of the zero padded signal is then executed as indicated at block 190. The complex conjugate of the signal spectrum generated as a result of the FFT is calculated as block 194 indicates. Similarly, the spectrum of one of the zero padded templates is determined by Fast Fourier Transform as indicated at 196. DSP 66 then calculates the cross correlation function of the signal spectrum and the template spectrum as shown at block 199. The cross correlation function is then multiplied by a Hanning window function as indicated at block 202 in order to deemphasize extreme frequencies. The resulting function is then converted to a time domain function by carrying out an Inverse Fast Fourier Transform as block 205 shows. The resulting time domain function is then smoothed at 207 in the same manner as described earlier with reference to block 165. As block 210 shows, the smoothed function is then reduced to 512 bytes. This is done simply by discarding every other data point in the 1024 byte sequence. A threshold value is then calculated in accordance with block 212. In the preferred embodiment, the threshold equals one-half the difference between the minimum and maximum values of the reduced function of block 210. The reduced function of block 210 is then compared with this threshold value. As indicated at decision block 215, the program then checks to determine whether there is a match between the signal and the template. While other techniques known to those skilled in the art could readily be used, this checking is carried out in the preferred embodiment by comparing the magnitude of each byte of the reduced function of block 210 with the threshold value calculated at block 212. Each byte of the reduced function is then transformed by setting its value to zero if its magnitude is initially less than the threshold and by setting its value to unity if its magnitude is initially greater than the threshold. Only if the above transformation results in a unit pulse of at least a predetermined number of successive bytes is a match between the signal and the template considered to be found. If no match is found, flow is redirected to block 196 for the next template to be compared with the signal. If a match is found, a control signal which corresponds uniquely to the template which has been matched by the signal is transmitted to the device 44 to be controlled as indicated at block 220. Preferably, the control signal is transmitted directly from digital signal processor 62 to device 44 by way of a second communication path 66 which does not include computer 55. Alternatively, the appropriate control signal may be routed from digital signal processor 62 to device 44 by way of computer 55 through cable 54 and communication link 60. It is desirable however to disconnect and remove computer 55 from apparatus 40 after templates have been developed in order to reduce the bulk and complexity of apparatus 40 when it is being used for controlling device 44. To do so, templates developed using computer 55 as well as the Hanning window used in the routine of FIG. 7 are stored on EPROMS received in memory device sockets associated with digital signal processor 62.

While the foregoing constitutes a preferred embodiment of the invention, it is to be understood that the invention is not limited to this preferred embodiment and that the preferred embodiment is shown for purposes of illustration. In light of the present disclosure, various alternative embodiments will become apparent to persons skilled in the art. Accordingly, it is to be recognized that changes in the selection and arrangement of components or data processing techniques can be made without departing from the scope of the invention as particularly pointed out and distinctly claimed in the claims appended and all legal equivalents thereof.

What is claimed is:

1. A sensor comprising:

an electrically conductive inner surface;

an electrically conductive continuous middle surface spaced from and surrounding said inner surface in a plane;

an electrically conductive continuous exterior surface spaced from and surrounding said middle surface in said plane; and an electrical conductor electrically connecting said inner surface to said exterior surface, said conductor, said exterior surface and said inner surface all being formed of a single, unitary piece of electrically conductive material.

2. The sensor of claim 1, wherein said conductive surfaces are formed from a unitary blank of electrically conductive material.

3. The sensor of claim 2, wherein said blank is formed by stamping.

4. The sensor of claim 2, wherein said blank is formed by etching.

5. The sensor of claim 2 wherein at least a portion of said blank is encapsulated in an electrically non-conductive material.

* * * * *